United States Patent [19]
Zanini-Fisher et al.

[11] Patent Number: 5,531,879
[45] Date of Patent: Jul. 2, 1996

[54] HEGO SENSOR WITHOUT CHARACTERISTIC SHIFT DOWN

[75] Inventors: Margherita Zanini-Fisher, Bloomfield Township; Richard E. Soltis, Redford; Eleftherios M. Logothetis, Birmingham; Carlos M. Barrera, Milford, all of Mich.

[73] Assignee: Ford Motor Company, Dearborn, Mich.

[21] Appl. No.: 498,453

[22] Filed: Jul. 5, 1995

[51] Int. Cl.⁶ .................................................. G01N 27/26
[52] U.S. Cl. ........................ 204/427; 204/424; 204/421
[58] Field of Search .................................. 204/421, 425, 204/426, 427, 428, 429, 424

[56] References Cited

U.S. PATENT DOCUMENTS

| | | | |
|---|---|---|---|
| 4,481,303 | 11/1984 | McIntyre et al. | 204/294 |
| 4,828,673 | 5/1989 | Maeda | 204/427 |
| 5,271,821 | 12/1993 | Ogasawara et al. | 204/428 |

*Primary Examiner*—Bruce F. Bell
*Attorney, Agent, or Firm*—Peter Abolins; Roger L. May

[57] ABSTRACT

A non-catalytic metal is used as an inner electrode of a heated exhaust gas oxygen sensor to eliminate the negative shift produced in the sensor emf when rich exhaust leaks into the reference compartment.

7 Claims, 3 Drawing Sheets

THE EFFECT OF CHARACTERISTIC SHIFT DOWN

HEGO SENSOR WITHOUT CHARACTERISTIC SHIFT DOWN

BACKGROUND OF THE INVENTION

1. Field of the Invention

This invention relates to electronic engine control of internal combustion engine operation.

2. Prior Art

Exhaust gas oxygen sensors have been used for many years for feedback control of the air-to-fuel ratio. The sensor has two catalytic noble metal electrodes, the outer electrode exposed to the exhaust gas and the inner electrode to the ambient air as a reference.

If $P_{O,o}$ and $P_{O,i}$ are the partial pressures of oxygen in the gases in contact with the outer and the inner electrodes, respectively, the sensor develops an emf given by the Nernst equation:

$$emf=RT/4F \ln(P_{O,i}/P_{O,o})$$

where, R, T, and F are respectively the ideal gas constant, the absolute temperature, and the Faraday constant.

FIG. 2 shows the partial pressure of oxygen $P_O$ in the exhaust gas as a function of air-to-fuel ratio. The solid line corresponds to the case that the exhaust gas is in thermodynamic equilibrium at a given temperature (700° C. in FIG. 2). The main feature is the abrupt and large change of $P_O$ at the stoichiometric A/F ratio. In contrast, the partial pressure of the free oxygen depicted by the dotted lines does not change significantly at stoichiometry and varies depending on the quality of the combustion in the cylinders of the engine. It is apparent that a unique relationship between partial pressure of oxygen and A/F exists only for the case of thermodynamic equilibrium.

It is important that the outer electrode of the sensor is sufficiently catalytic as to bring the exhaust gas close to the thermodynamic equilibrium at the sensor surface. This is the reason for using catalytic noble metals such as platinum and palladium as materials for the electrodes of the sensors. FIG. 3 shows typical HEGO sensor output as a function of A/F for noble metal catalytic electrodes.

Although HEGO sensors have been used successfully for years, several problems have occasionally arisen. One of these problems is the loss of the air reference atmosphere as a result of rich exhaust gas leaking into the air reference compartment through the exhaust gas seal. Two of the main causes responsible for this loss of air reference are the replacement of the metal seal with an electrically insulating ceramic seal which cannot be entirely impervious to gaseous species and the need to make the sensor water-submersible which severely limits the amount of air that can enter the air compartment from the ambient atmosphere. As a result, the oxygen concentration in the reference compartment can be temporarily depleted when the exhaust gas leak becomes sufficiently high because the catalytic inner electrode equilibrates the combustible species leaking from the exhaust side with the oxygen of the reference compartment. Under these conditions, for rich air-to-fuel mixtures, $P_{O,i}$ and $P_{O,o}$ are both very small and of the same order of magnitude. Consequently, the sensor emf has a small value. For lean air-to-fuel mixtures, $P_{O,i}$ is many orders of magnitude smaller than $P_{O,o}$ and the emf has a large negative value (FIG. 4). This negative shift of the sensor emf vs air-to-fuel ratio is called Characteristics Shift Down.

When the engine is operated in closed-loop control, the air-to-fuel ratio is alternately increased and decreased in time by monitoring when the output of the oxygen sensor crosses the 450 mV setpoint (or similarly calibratable value), which corresponds to stoichiometry in a fully functional device. However, when contamination of the air reference compartment occurs, the sensor emf always remains below the 450 mV value regardless of the air-to-fuel ratio in the exhaust because of the CSD effect. When this happens, the engine controller assumes that the engine is operating leaner than stoichiometry and attempts to compensate for it by shifting the air-to-fuel ratio to the maximum rich allowed value. Emissions are affected under this mode of operation and a MIL indicator is lit to signal the lack of HEGO switching as required by OBD II.

The present invention deals with a method to prevent the air reference from losing its oxygen concentration and prevent malfunctions of the engine control system.

SUMMARY OF THE INVENTION

An embodiment of this invention includes an exhaust gas oxygen sensor with a non-catalytic inner electrode. This keeps the oxygen pressure in the air reference compartment relatively high because a non-catalytic electrode can not bring the gas to thermodynamic equilibrium even when a large amount of rich exhaust gas leaks into the compartment.

DETAILED DESCRIPTION OF THE INVENTION

Figure 1:
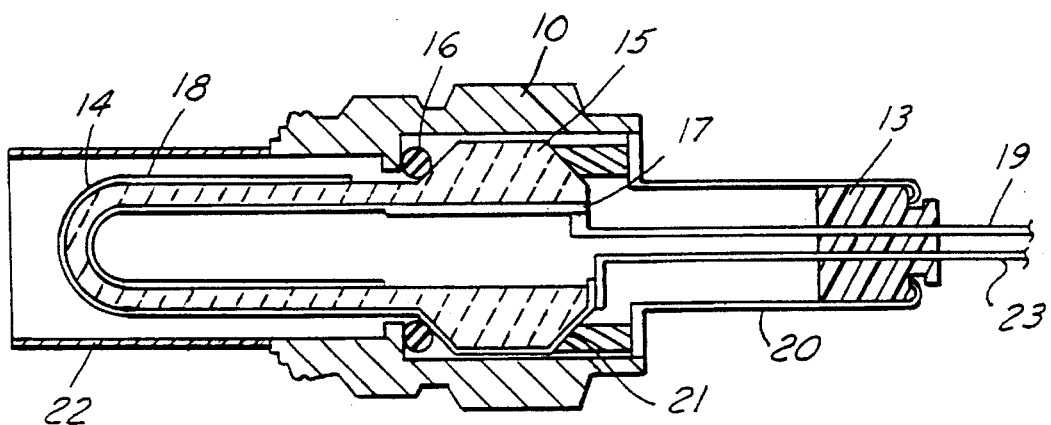
FIG. 1 is a cross sectional schematic of an automotive exhaust gas oxygen sensor in accordance with an embodiment of this invention.

Referring to the schematic of an automotive $ZrO_2$ oxygen sensor shown in FIG. 1, the sensor includes a $ZrO_2$ ceramic in the form of a hollow cylindrical tube 15 closed at one end. The $ZrO_2$ ceramic tube 15 has an exhaust gas electrode 14 on an outer surface and an air reference electrode 18 on an inner surface. Exhaust gas electrode 14 is made from a catalytic noble metal such as platinum. Air reference electrode 18 is made of a non-catalytic material and contacts with a sensor output lead 19 through a conductor 17. Exhaust gas electrode 14 contacts output lead 23 through a conductor 21. The $ZrO_2$ ceramic tube 15 is sealed onto an 18 mm annular spark plug shell 10 with a seal 16. Shell 10 has attached to one of its ends a cylindrical tube 20 which is closed off at the end with an electrically insulating cap 13. A protection tube 22 is attached on the other end of shell 10. The components of the sensor are substantially concentric around the axis of the sensor except for internal conductors 17 and 21.

Figure 2:
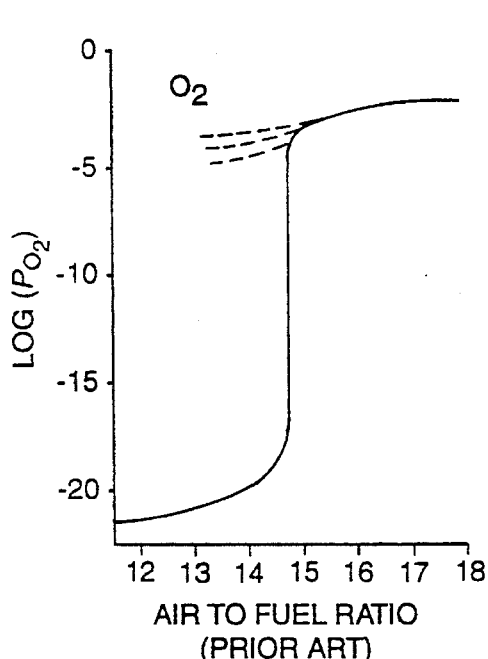
FIG. 2 is a graph that depicts the dependence of the oxygen partial pressure of the exhaust gas on the air-to-fuel ratio of an engine in accordance with the prior art.

In accordance with an embodiment of this invention, the sensor of FIG. 1 has air reference electrode 18 to act as one electrode for the $ZrO_2$ oxygen sensor while not acting as a catalyst in promoting any reaction altering the oxygen content of the adjacent gas. Even when a large amount of rich exhaust gas leaks into an air reference compartment adjacent air reference electrode 18 and the gas there becomes overall rich (corresponding to low $P_O$ under thermodynamic equilibrium conditions), the oxygen pressure in this compartment remains relatively high because the non-catalytic air reference electrode 18 can not bring the gas to thermodynamic equilibrium. That is, $P_{O,i}$ in the Nernst equation has a value close to that of the free oxygen (FIG. 2).

Figure 3:
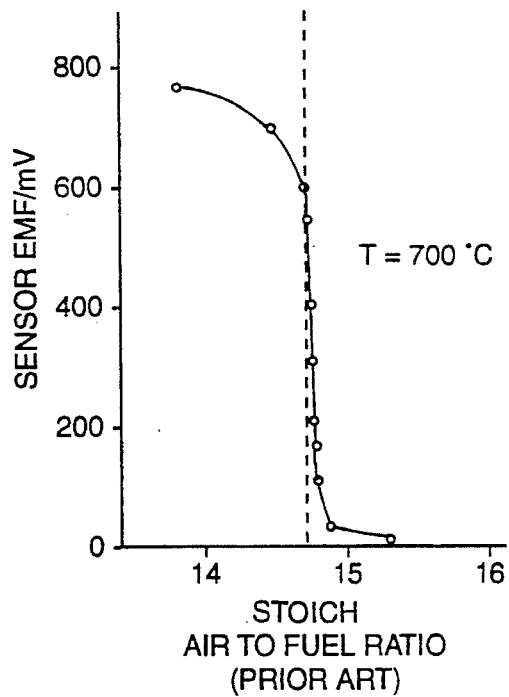
FIG. 3 is a graph that depicts the dependence of the voltage output of a normal sensor on the air-to-fuel ratio of an engine at 700 degrees Celsius in accordance with the prior art.
Figure 4:
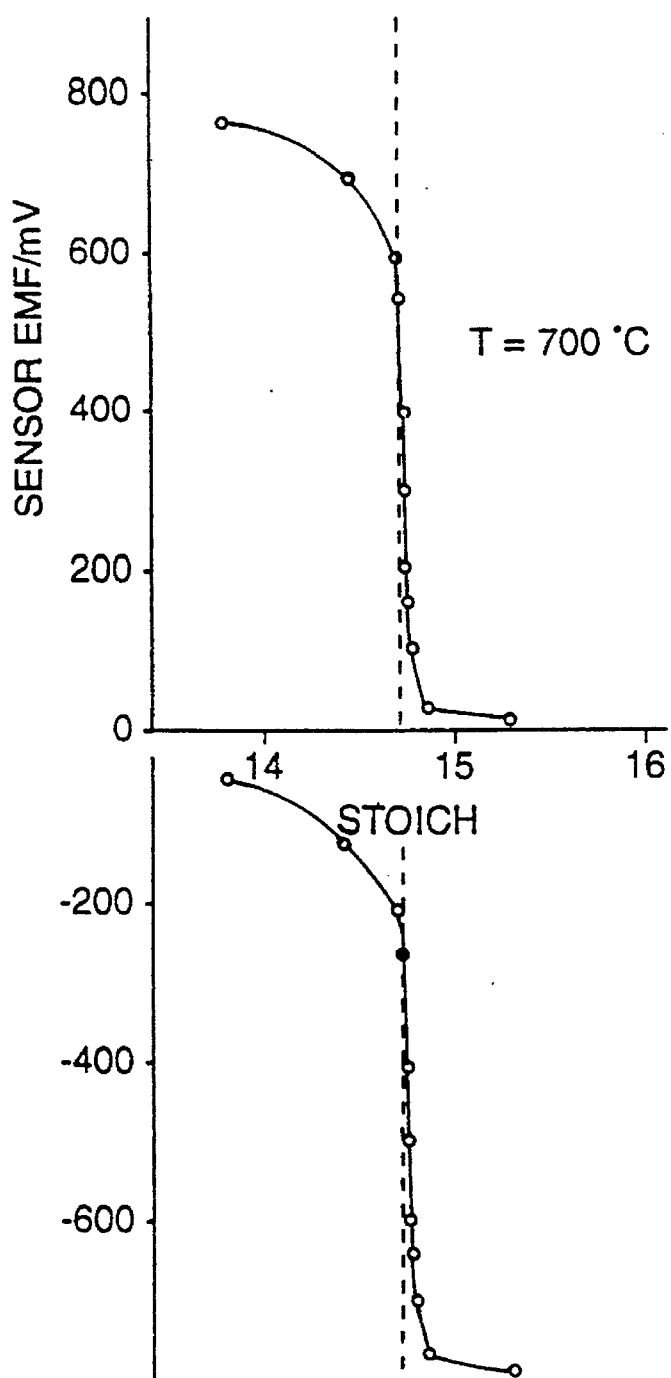
FIG. 4 is a graph that depicts the dependence of the voltage output of the normal sensor shown in FIG. 3 on air-to-fuel ratio together with a graph that depicts the dependence of the voltage output of a sensor with CSD as a function of air-to-fuel ratio at the same temperature.

Under these conditions, the emf vs A/F sensor characteristic remains essentially the same as in FIG. 3. Examples of non-catalytic electrodes that can be used according to the present invention include gold and gold/platinum electrodes. A non-catalytic electrode can also be formed by chemical poisoning of a noble metal catalytic electrode, e.g. by Pb contamination. However, this type of a non-catalytic electrode may not be adequate for an automotive device because Pb poisoning of catalytic metals tends to be partially reversible.

Figure 5:
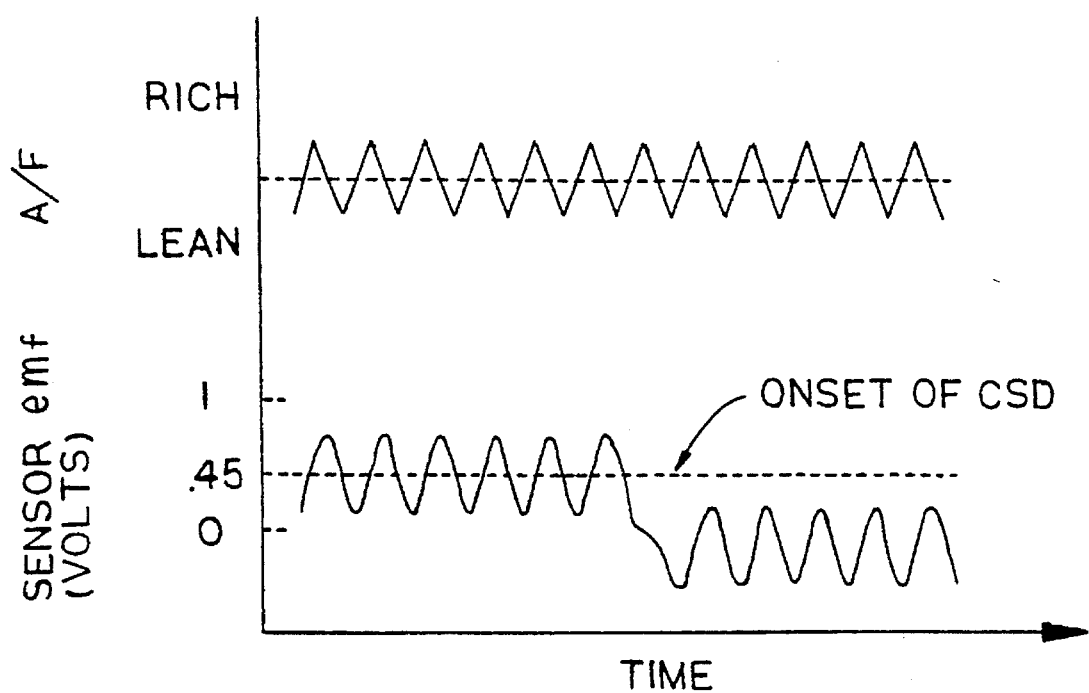
FIG. 5 is a graph that depicts the effects of CSD on the sensor emf when the air-to-fuel ratio is modulated in time.

FIG. 5 is a graphical representation of the output of a sensor exposed to an exhaust gas mixture continuously changing from lean-to-rich-to-lean air-to-fuel ratio values typically observed in automotive exhaust. In present production sensors, oxygen depletion in the air reference chamber produces a negative shift in the sensor output (CSD). As a result, the sensor emf always remains below 450 mV even for maximum rich values typically observed in exhaust.

Various modification and variations will no doubt occur to those skilled in the arts to which this invention pertains. Such modifications which basically rely on the teachings through which this disclosure has advanced the art are properly considered with the scope of this invention.

We claim:

1. An exhaust gas oxygen sensor for use with an internal combustion engine producing an exhaust gas said sensor including an outer electrode exposed to the exhaust gas and an inner reference electrode exposed to ambient air as a reference, said inner reference electrode being formed of a non-catalytic material.

2. An exhaust gas oxygen sensor as recited in claim 1 wherein said inner reference electrode is composed of gold.

3. An exhaust gas oxygen sensor as recited in claim 1 wherein the inner electrode includes gold and platinum.

4. An exhaust gas oxygen sensor for use with an internal combustion engine producing an exhaust gas flow, including:

an outer electrode adjacent the exhaust gas flow and an inner electrode adjacent a reference compartment;

said reference compartment bounded at least partly by said inner electrode;

said outer electrode being exposed to the exhaust gas and made of a catalytic material, and being sufficiently catalytic to bring the exhaust gas close to the thermodynamic equilibrium at the sensor surface; and said inner electrode formed of a non-catalytic material and exposed to the ambient air as a reference, to keep the oxygen partial pressure in the air reference compartment higher because such non-catalytic electrode cannot bring the gas to thermodynamic equilibrium even when rich exhaust gas is present in the compartment.

5. An exhaust gas oxygen sensor as recited in claim 4 wherein said inner electrode of formed of gold.

6. An exhaust gas oxygen sensor as recited in claim 5 wherein said inner electrode also includes platinum.

7. An exhaust gas oxygen sensor for use with an internal combustion engine producing an exhaust gas flow, including:

an outer electrode adjacent the exhaust gas flow and an inner electrode adjacent a reference compartment;

said reference compartment bounded at least partly by said inner electrode;

said outer electrode being exposed to the exhaust gas and made of a catalytic material, and being sufficiently catalytic to bring the exhaust gas close to the thermodynamic equilibrium at the sensor surface; and said inner electrode formed of a material including gold and exposed to the ambient air as a reference, to keep the oxygen partial pressure in the air reference compartment higher because such inner electrode cannot bring the gas to thermodynamic equilibrium even when rich exhaust gas is present in the compartment.

* * * * *